United States Patent [19]

Sibalis

[11] Patent Number: 4,557,723
[45] Date of Patent: Dec. 10, 1985

[54] APPLICATOR FOR THE NON-INVASIVE TRANSCUTANEOUS DELIVERY OF MEDICAMENT

[75] Inventor: Dan Sibalis, Stony Brook, N.Y.

[73] Assignee: Drug Delivery Systems Inc., New York, N.Y.

[21] Appl. No.: 524,252

[22] Filed: Aug. 18, 1983

[51] Int. Cl.⁴ .............................................. A61N 1/30
[52] U.S. Cl. ...................................... 604/20; 128/798
[58] Field of Search .............. 128/798, 802, 803, 82.1; 604/20

[56] References Cited

U.S. PATENT DOCUMENTS

| | | |
|---|---|---|
| 385,567 | 7/1888 | Hoke . |
| 486,902 | 11/1892 | Shults . |
| 588,479 | 8/1897 | Roedel .................. 604/20 |
| 2,493,155 | 1/1950 | McMillan .............. 604/20 |
| 2,667,162 | 1/1954 | Zwahlen ................ 604/20 |
| 2,784,715 | 3/1957 | Kestler .................. 604/20 |
| 3,163,166 | 12/1964 | Brant et al. ............ 604/20 |
| 3,289,671 | 12/1966 | Troutman et al. .... 604/20 |
| 3,547,107 | 12/1970 | Chapman et al. .... 128/640 |
| 4,008,721 | 2/1977 | Burton .................. 128/798 |
| 4,141,359 | 2/1979 | Jacobsen et al. ..... 604/20 |
| 4,239,046 | 12/1980 | Ong ..................... 128/798 |
| 4,243,052 | 1/1981 | Bailey .................. 128/798 |
| 4,250,878 | 2/1981 | Jacobsen et al. ..... 604/20 |
| 4,273,135 | 6/1981 | Larimore et al. .... 128/802 |
| 4,314,554 | 2/1982 | Greatbatch .......... 604/20 |
| 4,325,367 | 4/1982 | Tapper ................. 604/20 |
| 4,367,745 | 1/1983 | Welage ................ 128/798 |
| 4,406,658 | 9/1983 | Lattin et al. ......... 604/20 |
| 4,419,091 | 12/1983 | Behl et al. ............ 128/798 |
| 4,474,570 | 10/1984 | Ariura et al. ........ 128/798 X |

FOREIGN PATENT DOCUMENTS 2104388 3/1983 United Kingdom ................ 604/20

Primary Examiner—Lee S. Cohen
Attorney, Agent, or Firm—Lackenbach Siegel Marzullo Presta & Aronson

[57] ABSTRACT

An applicator for the electrophoretic deposition of a medicament through or on a skin surface. The device consists of layers of a reservoir containing the drug, a battery layer superimposed on the reservoir, and a cover of electrically conductive material fully enclosing the layers and having a lip along its periphery to engage the skin surface. An electrically conductive adhesive bonds the lip of the cover to the skin.

8 Claims, 4 Drawing Figures

U.S. Patent   Dec. 10, 1985   4,557,723
FIG. 1
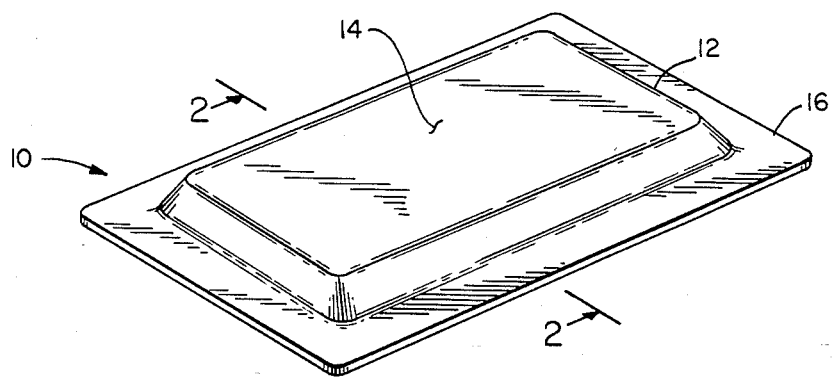
FIG. 2
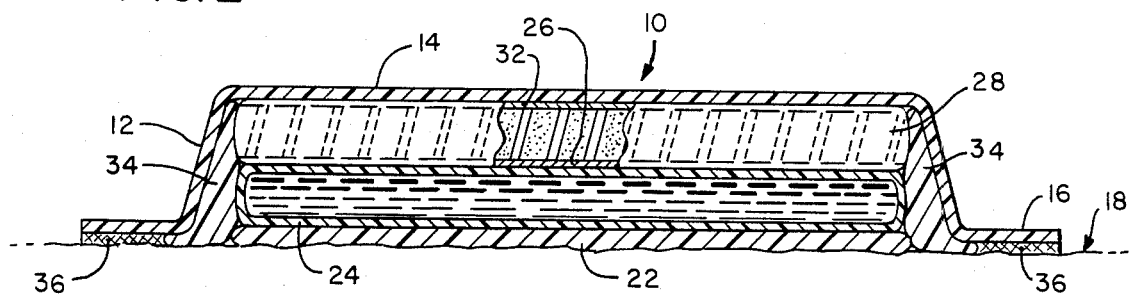
FIG. 3
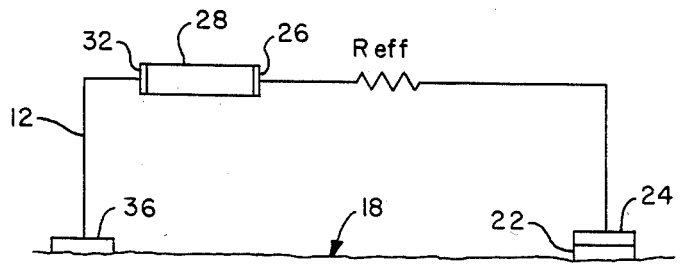
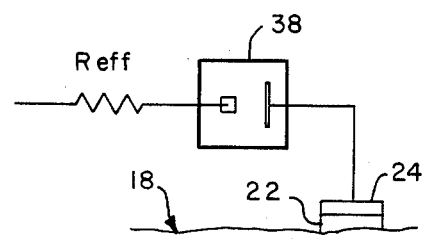
FIG. 4

APPLICATOR FOR THE NON-INVASIVE TRANSCUTANEOUS DELIVERY OF MEDICAMENT

BACKGROUND OF THE INVENTION

This invention relates to an applicator for the non-invasive transcutaneous delivery of a medicament and more particularly to a self-contained electrophoretic applicator of compact and conformable design for the controlled delivery of a medicament.

The delivery of medicament through a person's skin utilizing electrophoresis is well known where the drug is one whose molecules are ionic in solution or suspension. The solution or suspension is made subject to an electric field and if the electrode having the same charge as that of the ions is above the solution adjacent the skin which is the site of administration, the ions will be repelled and migrate through the skin into the blood stream.

A variety of problems associated with this technique have limited severely the extent of its use even though in many cases it is highly advantageous to be able to deliver the drug at a controlled rate. Equipment available for the electrophoretic administration of a medicament is generally bulky and expensive thereby largely limiting its use to medical offices requiring the attention of technicians. Reference to or disclosure of such apparatus is shown in the following U.S. Patents where it will be noted that there is great emphasis in developing electrodes which are disposable and/or more effective:

| | | |
|---|---|---|
| 2,492,155 | 4,141,359 | 4,250,878 |
| 3,163,166 | 4,166,457 | 4,273,135 |
| 3,289,671 | 4,239,052 | 4,367,745 |
| 3,677,268 | 4,243,052 | |

It will be noted from U.S. Pat. Nos. 3,289,671 and 4,141,359, in particular, that rate of drug delivery is a function of current flow and that control over current flow is crucial to having the correct amount of medicament applied.

Inasmuch as it is seen that the use of this electrotherapy is limited to medical facilities, the costs involved in this mode of treatment are a direct function of the time spent using the equipment, i.e., the time it takes to administer the medicament. Consequently there is great emphasis on delivering the drug as quickly as possible, resorting to the highest permissible rate of current flow. The most effective application of systemic drugs is where it is delivered into the blood stream at a very constant and low rate over a long period of time, i.e., perhaps from one or more hours up to days. In such a situation it is seen that present apparatus and methods for using electrophoresis for the application of medicaments are just not feasible.

There have been attempts to provide apparatus for such electrotherapy which is self-contained, so that the patient can wear the device carrying on normal activities while the drug is being administered. Devices of this type are disclosed in U.S. Pat. Nos. 385,556, 486,902, and 2,784,715. These devices are bulky, expensive, and do not provide for adequate control over the rate of delivery nor time over which the drug is delivered.

SUMMARY OF THE PRESENT INVENTION

The present invention overcomes or reduces many of the drawbacks of previous devices and methods for utilizing electrophoresis for the non-invasive transcutaneous delivery of a medicament.

This is accomplished in accordance with the principles of this invention by enclosing a complete electrophoretic drug administration system within an applicator virtually indistinguishable when in place from an adhesive bandage. The applicator is extremely shallow, capable of being made with a thickness of only about a tenth of an inch, and its length and width would be determined by the desired rate of drug delivery.

One preferred embodiment of this invention consists of a compact, multilayered applicator having a first active layer containing medicament in contact with the skin, a second active layer superimposed on the first comprising a member to make electrical contact with the skin through the first layer, and a third active layer superimposed on the second layer comprising the electrical battery for the applicator in electrical contact with the second layer. Other layers may be included to provide other functions to be described. The assembly just described is enclosed within a cover of electrically conductive material having a lip extending outwardly from the first layer and leaving the latter exposed and in contact with the skin. The underside of the lip is coated with an electrically conductive adhesive material so that when the applicator is mounted on the skin the cover material surrounded by the lip is in contact with the skin. The lip acts as a return electrode so that the skin completes the electrical circuit when the applicator is applied causing current to flow and medicament to be moved through the skin into the blood stream.

All of the layers of the applicator may be made from conformable material so that the applicator is capable of being made large enough to be mounted over wide areas regardless of the contour involved.

Features which may be included in the applicator as described above include provision to insure a constant current flow and a device to terminate drug delivery after a predetermined period of time or quantity of drug.

It is thus a principal object of this invention to provide self-contained apparatus and a method for the electrophoretic deposition of a medicament at a controlled rate.

Other objects and advantages of this invention will hereinafter become obvious from the following description of preferred embodiments of this invention.

BRIEF DESCRIPTION OF THE FIGURES

FIG. 1 is an isometric view of an applicator embodying the principles of this invention.

FIG. 2 is a section view along 2—2 of FIG. 1 showing the applicator mounted on skin.

FIG. 3 is a schematic of electrical circuitry incorporated in the embodiment shown in FIGS. 1 and 2.

FIG. 4 is an alternative arrangement for the circuit shown in FIG. 3.

DESCRIPTION OF THE PREFERRED EMBODIMENTS

Referring to FIGS. 1 and 2, applicator 10 consists of an outer cover 12 having a raised portion 14 and a lip 16 along the outer periphery. It is understood that applicator 10 can have any convenient shape or size, for example, square, rectangular, oval, circular, or tailored for a specific location on the skin, as long as this is a raised central portion to accommodate the rest of the electrophoresis unit to be described and the lip along its periphery.

As seen in FIG. 2, where applicator 10 is mounted on the surface of skin 18 of a patient, enclosed within the raised portion 14 of cover 12 are several layers to be described. The first layer is a microporous or semipermeable membrane 22 through which the medicament migrates to be deposited on skin 18. As will be noted from the following discussion, membrane 22 may not be needed depending on the nature of the reservoir for the medicament.

The second layer consists of a flexible pouch or reservoir 24 containing the drug to be administered. As is understood in the art, and shown in one or more of the U. S. patents identified above, reservoir 24 can be a pouch containing the drug of choice in solution or suspension, the walls of which are sufficiently dense to prevent leakage of the drug under ambient conditions, but sufficiently porous to permit migration of the charged particles or ions under the influence of the electric field imposed. It should be noted that it would be appropriate to employ the microporous membrane 22 when leakage under ambient conditions could occur, for example, as a result of packing of the applicators for shipment or storage, fluctuating temperatures, and possibly puncture of the reservoir. Also, the use of the membrane 22 could depend in large measure on the nature of the medicament involved. In the alternative, reservoir 24 can consist of porous material in which the drug is impregnated rather than a pouch containing the liquid medicament.

The third or next layer above reservoir 24 is an extended contact 26 which could be incorporated as one face of battery 28 which is the next layer. Contact 26 could be any suitable conductive material, preferably conformable to permit applicator 10 to be curved or bent to conform to the shaped surface of the skin. Suitable materials of this type are well known in the art and include electrically conductive polymers, preferable non-ionic. Carbon loaded or surface metalized plastics are also available for such use.

Battery 28 comprising the next layer can be made up of a group of cells internally connected in series to obtain the desired voltage necessary to obtain the electrophoretic action with the particular medicament. Orientation of battery 28 would depend on whether the charged (ionic) particles of the drug of choice are positive or negative. If the partices are negatively charged in solution or suspension then contact 26 would be connected to the negative side of battery 28 as the skin will then be positive with respect to that contact and will attract the ions. With regard to battery 28, it should be noted that any conventional miniaturized battery cells now generally available can be employed, arranged and connected in series to obtain the desired operating voltage. In addition, the technology now exists for batteries which are made up of very thin, flexible sheets of a conductive polymer with high surface areas relative to thickness to provide adequate current densities. One such so-called plastic battery is described in "Batteries Today", Autumn 1981, pages 10, 11, and 24. When such a battery is employed, sheets may be layered to place the cells in series, and an effective compromise between number of sheets and surface areas of sheets is to layer them in a diagonal as shown somewhat schematically in FIG. 2. Of course, battery selection would ultimately depend on such factors as the degree of conformability desired, voltage and current densities required for a specific application, and time of discharge.

Layered above battery 28 would be another contact 32 which could be similar in construction to that of contact 26 and connected electrically to the opposite side of battery 28.

Cover 12 which encloses all of the layers of applicator 10 is made from a flexible conductive plastic material such as a polymer impregnated with carbon or surface metalized plastic. Insulating material 34 fills the space between the side wall of raised portion 14 and the various layers contained therein.

An electrically conductive adhesive material 36 coats the underside of lip 16 so that applicator 10 may be placed on and adhere to skin 18 and make good electrical contact.

It will be seen that the above described arrangement forms a complete electric circuit from one side of battery 28, cover 12, adhesive material 36, skin 18, microporous membrane 22, liquid reservoir 24, and back to battery 28.

For a more particular description of the electrical circuit formed by the arrangement just described, reference is made to FIG. 3 wherein the circuit is shown schematically with numerals corresponding to the structure shown in FIGS. 1 and 2.

Battery 28 is connected through contact 32, cover 12, and adhesive layer 36 to skin 18. The other side of battery 28 is connected electrically through contact 26, liquid reservoir 24 and membrane 22 to skin 18 to complete the circuit. Resistor Reff represents the effective resistance of the complete circuit, including skin 18, the adhesive layer 36, cover 12, battery 28 and its contacts 26 and 32, as well as reservoir 24 and membrane 22, In a system of this type, one of the aims is to establish a very low rate of current flow so that the medicament will be deposited slowly over a long period of time. Current flow of down as low as 0.0001 ampere-hour per square centimeter of skin surface below membrane 22 is a typical current which may be selected for the application of a particular drug. Electrical resistance of the skin to current flow is of the order of 6-9 K ohms and is roughly independent of the distance between the points on the skin where electrical contact is made. This is because skin electrical resistance is largely that of resistance to penetration, the current flowing through the fluids of the body in which electrical resistance being very low. Thus, in order to establish current flow at the rate indicated, by ohm's law, it is seen that total resistance of the circuit using a 1.5 volt battery should be about 360 K ohms for each square centimeter of application. This resistance, the effective resistance, Reff, of the circuit, can be built into any one component or combination of components of the circuit shown in FIG. 3, including the battery resistance, electrodes, cover material, etc. In addition, if desired, in order to maintain current flow constant over the full period of operation a constant current limiting device can be made integral with and a part of conductor 26, or any other part of the circuit where it is found convenient to do so.

Furthermore, as indicated schematically in FIG. 4, applicator 10 may be designed to incorporate provision to insure that the deposit of medicament will cease after a given period of time or after a certain quantity of drug is administered. This can be accomplished by inserting in the circuit an integrating device such as a reverse plating cell 38. Cell 38, as is known in the art, comprises a pair of electrodes on which one is a coating of material to be transferred to the other electrode. When all of the plating material is deposited, after a predetermined period of time based upon the thickness of the original coating has lapsed, or integrated current flow representing the desired quantity of drug to be delivered, there is a large increase in internal resistance resulting in a substantial drop of current flow and an effective halt to drug migration. Such a device can be employed to establish in advance the period of time over which the medicament is to be applied or, as noted above, the quantity of the drug to be delivered. Cell 38 is a relatively high resistance device and could provide for much of the high resistance required for the operation of applicator 10.

Cell 38 may be made a part of contact 32 or be inserted between contact 32 and cover material 14. In addition, provision may be made for current flow to be built up gradually to avoid any shock to the recipient of the drug.

Applicator 10 may be prepared in advance, in different sizes and shapes, sealed within a plastic pouch, with a protective strip over its exposed side. Different drugs can be incorporated for particular applications, batteries may be varied to meet specific current flow requirements, and of course the electrical orientation of each battery would depend on the particular medicament. In the use of the device, the protective strip is removed and the applicator placed on the skin where desired such as behind the ear. Current flow starts immediately along with migration of the drug.

The use of the invention as herein described makes it possible for the first time to provide for drug therapy over an extended period of time with a degree of control and accuracy which heretofore has not been possible or practical. The cost of such therapy using this invention is reduced significantly with the result that extensive use of the invention will have a favorable economic impact on medical care.

While only certain preferred embodiments of this invention have been described, it is understood that many embodiments thereof are possible without departing from the principles of this invention as defined in the claims which follow.

What is claimed is:

1. An applicator for the migration of medicament through the skin into the blood stream of a patient comprising: reservoir means for containing said medicament, battery means for supplying a charge for the medicament and being adjacent one side of said reservoir means with the side of said battery means facing said reservoir means for charging the medicament, means for covering comprising an electrically conductive material for partially enclosing said battery means and said reservoir means leaving the side of said reservoir means opposite that of said battery means exposed for contacting said skin, means for electrically connecting the battery means to the cover means, said cover means having a lip defining the periphery of said applicator for making contact with said skin when mounted on said skin leaving said battery means and reservoir means fully enclosed, and electrically conductive adhesive material coating disposed on the underside of said lip, whereby when said applicator is mounted on said skin a complete electrical circuit through said skin is formed and the medicament in said reservoir means migrates out of said reservoir means and through said skin into the blood steam of said patient.

2. The applicator of claim 1 in which said reservoir means is made from a microporous material whereby said medicament provides an electrical path therethrough.

3. The applicator of claim 2 said covering an reservoir means being conformable to the shape of said skin.

4. The applicator of claim 3 having a semipermeable membrane within said cover means on the side of said reservoir means facing said skin.

5. The applicator of claim 4 having means within said cover means for electrically insulating the latter from said reservoir means.

6. The applicator of claim 2 said circuit having means to maintain constant current flow during the period said medicament is being delivered.

7. The applicator of claim 6 said circuit having means to terminate deposition of said medicament after a predetermined quantity of medicament is delivered.

8. The applicator of claim 7 in which the last named means is a reverse plating cell.

* * * * *